(12) United States Patent
Euliano et al.

(10) Patent No.: US 8,672,858 B2
(45) Date of Patent: *Mar. 18, 2014

(54) METHOD AND APPARATUS FOR PREDICTING WORK OF BREATHING

(75) Inventors: Neil R. Euliano, Gainesville, FL (US); Victor L. Brennan, Gainesville, FL (US); Paul B. Blanch, Gainesville, FL (US); Michael J. Banner, Alachua, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/400,371

(22) Filed: Feb. 20, 2012

(65) Prior Publication Data
US 2012/0215081 A1    Aug. 23, 2012

Related U.S. Application Data

(63) Continuation-in-part of application No. 12/499,576, filed on Jul. 8, 2009, which is a continuation of application No. 11/758,159, filed on Jun. 5, 2007, now Pat. No. 7,588,543, which is a continuation of application No. 10/652,992, filed on Aug. 29, 2003, now Pat. No. 7,425,201.

(60) Provisional application No. 60/407,099, filed on Aug. 30, 2002.

(51) Int. Cl.
*A61B 5/02* (2006.01)

(52) U.S. Cl.
USPC .......................................................... 600/529

(58) Field of Classification Search
USPC .......................................................... 600/529
See application file for complete search history.

(56) References Cited

U.S. PATENT DOCUMENTS

| 5,261,397 | A | * | 11/1993 | Grunstein | 128/204.18 |
| 5,316,009 | A | * | 5/1994 | Yamada | 128/204.23 |
| 5,490,502 | A | * | 2/1996 | Rapoport et al. | 128/204.21 |
| 5,682,881 | A |   | 11/1997 | Winthrop et al. | |

(Continued)

FOREIGN PATENT DOCUMENTS

| EP | 0 521 515 A1 | 1/1993 |
| WO | WO 01/00265 | 1/2001 |
| WO | WO 02/28281 | 4/2002 |

OTHER PUBLICATIONS

Banner et al. "Respiratory muscle loading and the work of breathing"*Journal of Cardiothoracic and Vascular Anesthesia*, Saunders, Philadelphia, PA, US, 1995, 192-204, vol. 9, No. 2.

(Continued)

*Primary Examiner* — Patricia Mallari
*Assistant Examiner* — Vasuda Ramachandran
(74) *Attorney, Agent, or Firm* — Saliwanchik, Lloyd & Eisenschenk

(57) ABSTRACT

A method of creating a noninvasive predictor of both physiologic and imposed patient effort of breathing from airway pressure and flow sensors attached to the patient using an adaptive mathematical model. The patient effort is commonly measured via work of breathing, power of breathing, or pressure-time product of esophageal pressure and is important for properly adjusting ventilatory support for spontaneously breathing patients. The method of calculating this noninvasive predictor is based on linear or non-linear calculations using multiple parameters derived from the above-mentioned sensors.

31 Claims, 4 Drawing Sheets

(56) References Cited

U.S. PATENT DOCUMENTS

| | | |
|---|---|---|
| 5,752,921 A | 5/1998 | Orr |
| 5,807,245 A | 9/1998 | Aldestam et al. |
| 5,876,352 A | 3/1999 | Weismann |
| 5,887,611 A | 3/1999 | Lampotang et al. |
| 5,941,841 A | 8/1999 | Mutch et al. |
| 5,953,713 A | 9/1999 | Behbehani et al. |
| 6,004,267 A | 12/1999 | Tewari et al. |
| 6,019,732 A | 2/2000 | Volgyesi |
| 6,027,498 A | 2/2000 | Mutch et al. |
| 6,058,322 A * | 5/2000 | Nishikawa et al. ............ 600/408 |
| 6,068,602 A | 5/2000 | Tham et al. |
| 6,083,173 A | 7/2000 | Grant et al. |
| 6,099,481 A | 8/2000 | Daniels et al. |
| 6,135,105 A * | 10/2000 | Lampotang et al. ..... 128/204.21 |
| 6,158,432 A | 12/2000 | Biondi et al. |
| 6,179,784 B1 | 1/2001 | Daniels et al. |
| 6,240,920 B1 * | 6/2001 | Strom ...................... 128/204.23 |
| 6,257,234 B1 | 7/2001 | Sun |
| 6,290,654 B1 | 9/2001 | Karakasoglu |
| 6,390,091 B1 * | 5/2002 | Banner et al. ............ 128/204.18 |
| 6,439,229 B1 | 8/2002 | Du et al. |
| 6,450,164 B1 | 9/2002 | Banner et al. |
| 6,629,934 B2 | 10/2003 | Mault et al. |
| 2003/0050568 A1 * | 3/2003 | Green et al. .................. 600/538 |

OTHER PUBLICATIONS

Banner et al., "Breathing Frequency and Pattern Are Poor Predictors of Work of Breathing in Patients Receiving Pressure Support Ventilation," *Chest*, 1995, vol. 108, pp. 1338-1344.

Leon et al., "Ventilation Mode Recognition Using Artificial Neural Networks," *Computers and Biomedical Research*, 1997, vol. 0, pp. 373-378.

Macintyre, "Weaning from Mechanical Ventilatory Support: Volume-Assisting Intermittent Breaths versus Pressure-Assisting Every Breath", *Respiratory Care*, 1988. vol. 33, No. 2, pp. 121-125.

Kirton et al. "Elevated imposed work of breathing masquerading as ventilator weaning intolerance" Chest, 1995; pp. 1021-1025, vol. 108, No. 4.

* cited by examiner

METHOD AND APPARATUS FOR PREDICTING WORK OF BREATHING

CROSS REFERENCE TO RELATED APPLICATIONS

This application is a continuation-in-part application of Ser. No. 12/499,576, filed Jul. 8, 2009; which is a continuation application of U.S. Ser. No. 11/758,159, filed Jun. 5, 2007, now U.S. Pat. No. 7,588,543; which is a continuation application of U.S. Ser. No. 10/652,992, filed Aug. 29, 2003, now U.S. Pat. No. 7,425,201; which claims the benefit of U.S. Provisional Application Ser. No. 60/407,099, filed Aug. 30, 2002, each of which is hereby incorporated by reference herein in its entirety.

FIELD OF THE INVENTION

The present invention relates generally to the field of respiratory therapy and physiology, including ventilator and respiratory monitor technology, and, more particularly, to a method and apparatus for predicting a patient's physiologic work of breathing and imposed work of breathing.

BACKGROUND

Mechanical ventilatory support is widely accepted as an effective form of therapy and means for treating patients with respiratory failure. Ventilation is the process of delivering oxygen to and washing carbon dioxide from the alveoli in the lungs. When receiving ventilatory support, the patient becomes part of a complex interactive system that is expected to provide adequate ventilation and promote gas exchange to aid in the stabilization and recovery of the patient. Clinical treatment of a ventilated patient often calls for monitoring a patient's breathing to detect an interruption or an irregularity in the breathing pattern, for triggering a ventilator to initiate assisted breathing, and for interrupting the assisted breathing periodically to wean the patient off of the assisted breathing regime, thereby restoring the patient's ability to breathe independently.

In those instances in which a patient requires mechanical ventilation due to respiratory failure, sleep apnea, post-operative care, or other situations, a wide variety of mechanical ventilators is available. Most modern ventilators allow the clinician to select and use several modes of inhalation either individually or in combination via the ventilator setting controls that are common to the ventilators. Some ventilators such as those designed for noninvasive ventilation (NIV) primarily utilize mask interfaces and can be very simple to operate with very few choices of settings, typically some baseline pressure level with or without a higher level of pressure support during inhalation.

The modes of breathing available in ventilators can be defined in three broad categories: spontaneous, assisted or controlled. During spontaneous ventilation without other modes of ventilation, the patient breathes at his own pace, but other interventions may affect other parameters of ventilation including the tidal volume and the baseline pressure, above ambient, within the system. In assisted ventilation, the patient initiates the inhalation by lowering the baseline pressure by varying degrees, and then the ventilator "assists" the patient by completing the breath by the application of positive pressure. During controlled ventilation, the patient is unable to breathe spontaneously or initiate a breath, and is therefore dependent on the ventilator for every breath. During spontaneous or assisted ventilation, the patient is required to "work" (to varying degrees) by using the respiratory muscles in order to breathe.

The total work of breathing (the work to initiate and sustain a breath) performed by a patient to inhale while intubated or attached to a ventilator may be divided into two major components: physiologic work of breathing (the work of breathing of the patient, "WOBp") and breathing apparatus (e.g., endotracheal tube or other form of patient interface and ventilator) imposed resistive work of breathing or imposed work of breathing ("WOBi"). The total work of breathing ("WOW") can be measured and quantified in Joules/L of ventilation. In the past, techniques have been devised to supply ventilatory therapy to patients for the purpose of improving patient's efforts to breathe by decreasing the total work of breathing to sustain the breath. Still other techniques have been developed that aid in the reduction of the patient's inspiratory work required to trigger a ventilator system "ON" to assist the patient's breathing. It is desirable to reduce the effort expended by the patient in each of these phases, because a high total work of breathing load can cause further damage to a weakened patient or be beyond the capacity or capability of small or disabled patients.

Furthermore, it is desirable to quantify the imposed work of breathing (WOBi) of a patient since this value is critical in the decision of when to extubate or remove ventilatory support from the patient. High work loads tend to create breathing patterns that are rapid and shallow (high frequency and low tidal volume). Rapid shallow breathing is typically a contra-indicator of extubation success. If this high work load, however, is caused mainly by a large imposed work of breathing such that most of the excess work is caused by the breathing apparatus, extubation success is much higher ("Elevated imposed work of breathing masquerading as ventilator weaning intolerance." *Chest* October 1995; 108(4): 10215).

The early generation of mechanical ventilators, prior to the mid-1960s, was designed to support alveolar ventilation and to provide supplemental oxygen for those patients who were unable to breathe due to neuromuscular impairment. Since that time, mechanical ventilators have become more sophisticated and complicated in response to increasing understanding of lung pathophysiology. In an effort to improve a patient's tolerance of mechanical ventilation, assisted or patient-triggered ventilation modes were developed. Partial positive pressure ventilation (PPV) support, in which mechanical support supplements spontaneous ventilation, became possible for adults outside the operating room when intermittent mandatory ventilation (IMV) became available in the 1970s. Varieties of "alternative" ventilation modes addressing the needs of severely impaired patients continue to be developed. Similarly, small, easy to use ventilators have been developed to support patients who need less support. These ventilators often utilize noninvasive mechanisms (masks, nasal cannulas, full-head bags, etc.) to interface to the patient.

In recent years, microprocessors have been introduced into modern ventilators. Microprocessor ventilators are typically equipped with sensors that monitor breath-by-breath flow, pressure, volume, and derive mechanical respiratory parameters. Their ability to sense and transduce "accurately," combined with computer technology, makes the interaction between clinician, patient, and ventilator more sophisticated than ever. The prior art microprocessor controlled ventilators suffered from compromised accuracy due to the placement of the sensors required to transduce the data signals. Consequently, complicated algorithms were developed so that the ventilators could "approximate" what was actually occurring within the patient's lungs on a breath-by-breath basis. In effect, the computer controlled prior art ventilators were limited to the precise, and unyielding, nature of the mathematical algorithms that attempted to mimic cause-and-effect in the ventilator support provided to the patient.

The overall performance of the assisted ventilatory system is determined by both physiological and mechanical factors. The physiological determinants, which include the nature of the pulmonary disease, the ventilatory efforts of the patient, and many other physiological variables, changes with time and are difficult to diagnose. Moreover, the physician historically had relatively little control over these determinants. Mechanical input to the system, on the other hand, is to a large extent controlled and can be reasonably well characterized by examining the parameters of ventilator flow, volume, and/or pressure. Optimal ventilatory assistance requires both appropriately minimizing physiologic workloads to a tolerable level and decreasing imposed resistive workloads to zero. Doing both should ensure that the patient is neither overstressed nor oversupported. Insufficient ventilatory support places unnecessary demands upon the patient's already compromised respiratory system, thereby inducing or increasing respiratory muscle fatigue. Excessive ventilatory support places the patient at risk for pulmonary-barotrauma, respiratory muscle deconditioning, and other complications of mechanical ventilation.

In addition to total work of breathing (WOB), there are other measurements of patient effort, including power of breathing (POB), the rate at which total work of breathing is done, and the pressure time product (PTP), the integrated product of time multiplied by the decrease in pleural pressure during a breath. These methodologies are similar in their goal of measuring patient effort, but are calculated differently and provide different measures of the patient effort.

Although total work of breathing (and its alternatives) has been considered an important parameter for appropriately setting a ventilator, it has remained largely unused because of the difficulty in obtaining its value. Physiologic work of breathing is defined using a pleural pressure versus volume graph of a patient's breath. The pleura is a two-layered membrane that envelops the lung and contains lubricating fluid between its inner and outer layers. During breathing, the respiratory muscles either compress or expand the lungs by exerting forces on the pleura. The pressure in the pleural space therefore represents the respiratory effort. The patient's physiologic work of breathing is the area from the chest wall compliance line on the right to the pleural pressure versus volume loop on the left (see FIG. 1). Since the pleural pressure is very difficult to obtain and may be different at different positions in the pleural space, a typical surrogate for pleural pressure is esophageal pressure. The esophageal pressure is typically obtained by placing a balloon in the esophagus between the heart and the stomach.

Likewise, although imposed work of breathing has been considered an important parameter for appropriately setting a ventilator, it has also remained largely unused because of the difficulty in obtaining its value. Imposed work of breathing is the area below baseline pressure circumscribed within the tracheal pressure-tidal volume loop during spontaneous inhalation. Typically, this is done by using a catheter inserted into the tracheal tube or a lumen in the side of the tracheal tube that opens at the distal end of the tracheal tube. These devices are then attached to a pressure transducer to measure tracheal pressure. The greatest single difficulty with these devices is the harsh environment in which they exist and their propensity for becoming clogged. For this and other reasons, tracheal pressure is difficult to reliably measure and thus is not normally used.

U.S. Pat. No. 5,316,009 describes an apparatus for monitoring respiratory muscle activity based on measuring resistance and elastance of the lung and then calculating a value called Pmus from the standard equation of motion where Paw=Pmus+R*flow+V/C. It also discloses calculation of a PTP of pmus, which is not the standard PTP, and a "work" Wmus, but not necessarily real WOB. A problem with the method taught by the '009 patent is that Pmus is difficult to measure in a spontaneously breathing patient because the parameters R and C must be very accurately computed in order for Pmus to correlate with "work". Moreover, R and C in a spontaneously breathing patient with ventilator support are very difficult to obtain accurately.

Occlusion pressure at 0.1 seconds after breath initiation by the patient (PO.1) has also been proposed as an indicator of work of breathing. PO.1 can be based on esophageal pressure or airway pressure. An esophageal pressure PO.1 is invasive but correlates fairly well with work of breathing. An airway pressure PO.1 is noninvasive, but does not correlate nearly as well with work of breathing.

A number of other patents exist for respiratory systems including U.S. Pat. Nos. 6,439,229; 6,390,091; 6,257,234; 6,068,602; 6,027,498; 6,019,732; 5,941,841; 5,887,611; 5,876,352; 5,807,245; and 5,682,881, incorporated herein by reference.

Accordingly, there is a need in the art for a system and method to noninvasively and accurately predict physiologic work of breathing and imposed work of breathing in a patient. The present invention is designed to address this need.

SUMMARY OF THE INVENTION

Broadly speaking, the present invention provides a method and apparatus for noninvasively predicting (estimating) physiologic work of breathing (the amount of effort expended by the patient to breathe) and imposed work of breathing (the amount of effort expended by the patient imposed by the breathing apparatus). This effort, typically invasively calculated as (imposed and/or physiologic) work of breathing (WOB), power of breathing (POB), or pressure time product (PTP), is useful in determining the most appropriate settings on a ventilator used to support the patient's breathing. Measuring patient effort allows for appropriate ventilatory support that avoids respiratory muscle fatigue and respiratory muscle deconditioning. Measuring imposed patient effort allows for more appropriate ventilatory support by allowing for the imposed effort to be driven to zero to simulate more natural breathing and also as an important extubation criteria.

In one aspect of the invention, the method comprises creating a mathematical model of the patient's inspiratory effort using predetermined parameters that are collected noninvasively, such as those collected with standard respiratory monitors. The respiratory monitors typically contain airway pressure and airway flow sensors that measure the flow going into and out of the patient, and often times a carbon dioxide sensor and pulse oximeter. From these time-waveforms, a variety of parameters are selectively derived that are used in characterizing different aspects of the patient's breathing and/or the patient's interaction with the ventilator. These parameters contain information that is extracted to accurately estimate the patient effort.

More specifically, the method of the invention comprises a method of estimating the actual patient effort parameter using a combination of multiple parameters derived from sensors that monitor the patient and/or ventilator. The patient effort parameter can be any parameter that represents the effort exerted by the patient to breathe, including but not limited to work of breathing, power of breathing, or pressure time product.

In this method, the parameters are preferably derived from the airway pressure, flow, and volume waveforms and the carbon dioxide and pulse oximeter waveforms normally collected by a respiratory monitor, including but not limited to tidal volume, breathing frequency, peak inspiratory pressure (PIP), inspiratory time, PO.1, trigger time, trigger depth, respiratory system resistance, respiratory compliance, end-tidal carbon dioxide, variations in the pulse oximeter plethysmogram, and the concavity/convexity of the pressure waveform.

This method includes using a linear combination of parameters or a nonlinear combination of parameters, including but not limited to a neural network, fuzzy logic, mixture of experts, or polynomial model. Moreover, multiple different models can be used to estimate the patient effort of different subsets of patients. These subsets can be determined by various means, including but not limited to patient condition (pathophysiology), patient physiologic parameters (lung resistance and compliance), or other parameters.

In a preferred aspect of the invention, the method for estimating work of breathing in a patient comprises use of a neural network, wherein the neural network provides work of breathing information for the patient based upon input data, wherein the input data includes at least one of the following parameters: the airway pressure, flow, airway volume, carbon dioxide flow, and pulse oximeter plethysmogram waveforms normally collected by a respiratory monitor, including but not limited to tidal volume, breathing frequency, peak inspiratory pressure (PIP), inspiratory time, PO1 (see reference), trigger time, trigger depth, respiratory system resistance, respiratory compliance, end-tidal carbon dioxide, variations in the pulse oximeter plethysmogram, and the concavity/convexity of the pressure waveform, wherein the work of breathing information is provided as an output variable.

In the above-noted method, the neural network is trained by clinical testing of a test population of patients to obtain teaching data, which includes the above-noted input information. The teaching data is provided to the neural network, whereby the neural network is trained to provide an output variable corresponding to the work of breathing. Teaching data further includes esophageal pressure and/or tracheal pressure.

As a system for estimating (imposed and/or physiologic) work of breathing in a patient, the system comprises a neural network that first receives as input primary teaching data obtained from clinical testing of a test population of patients, whereby the neural network learns the teaching data and is trained to provide an output variable for work of breathing, such that when the neural network receives patient input data in the form of the above-noted parameters obtained from a patient, the neural network provides the output variable for estimating work of breathing for that patient.

The invention can be implemented in numerous ways, including as a system (including a computer processing or database system), a method (including a computerized method of collecting and processing input data and a method for evaluating such data to provide an output(s)), an apparatus, a computer readable medium, a computer program product, or a data structure tangibly fixed in a computer readable memory. Several embodiments of the invention are discussed below.

As a system, an embodiment of the invention includes a processor unit having input and output devices. The processor unit operates to receive input parameters, process the input and provide an output corresponding to work of breathing. This output can be then used to control external devices, such as a ventilator. The processing of the data can be accomplished by various means such as neural networks, parallel distributed processing systems, neuromorphic systems, or the like.

As a method of predicting (imposed and/or physiologic) work of breathing, the method includes processing predetermined input variables (parameters), preferably through the use of a neural network.

As computer readable media containing program instructions, an embodiment of the invention includes: computer readable code devices for receiving input variables, processing the input, and providing an output indicative of work of breathing. In a preferred embodiment, processing comprises utilizing a neural network. The method may further include controlling a ventilator in response to the output obtained.

The methods of the present invention may be implemented as a computer program product with a computer-readable medium having code thereon. The program product includes a program and a signal bearing media bearing the program.

As an apparatus, the present invention may include at least one processor, a memory coupled to the processor, and a program residing in the memory that implements the methods of the present invention.

Other aspects and advantages of the invention will become apparent from the following detailed description taken in conjunction with the accompanying drawings, illustrating, by way of example, the principles of the invention.

All patents, patent applications, provisional applications, and publications referred to or cited herein, or from which a claim for benefit of priority has been made, are incorporated herein by reference in their entirety to the extent they are not inconsistent with the explicit teachings of this specification.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DESCRIPTION OF THE PREFERRED EMBODIMENT

Figure 1:
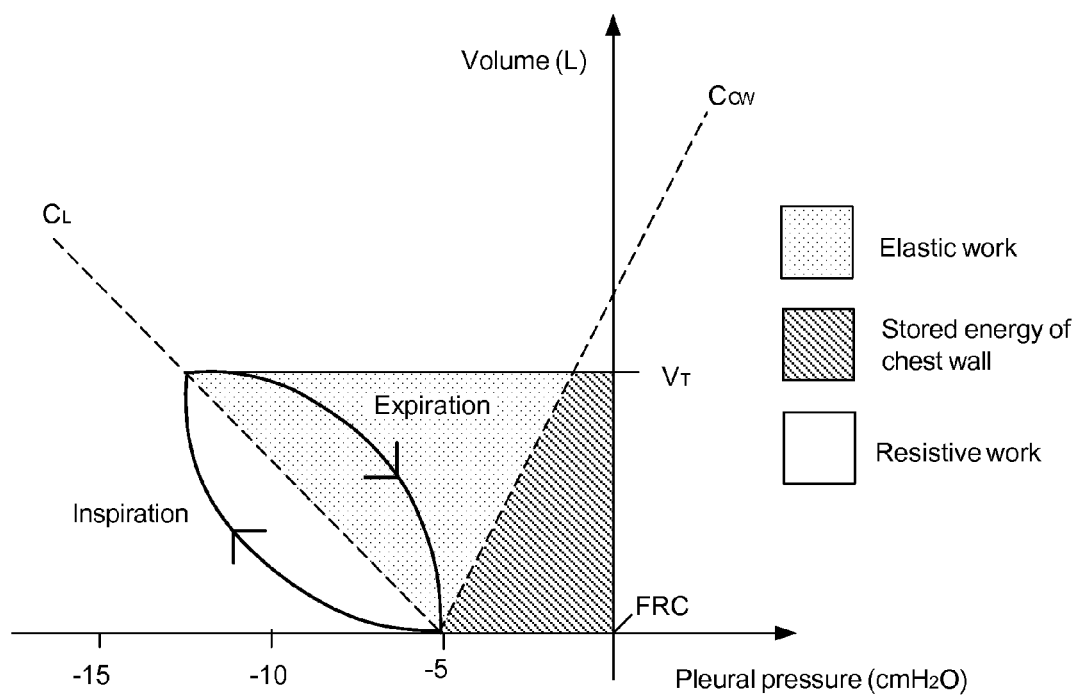
FIG. 1 is a graphical representation of pleural pressure showing elastic work, stored energy of chest wall and resistive work.

Referring now to the drawings, the preferred embodiment of the present invention will be described.

Figure 2:
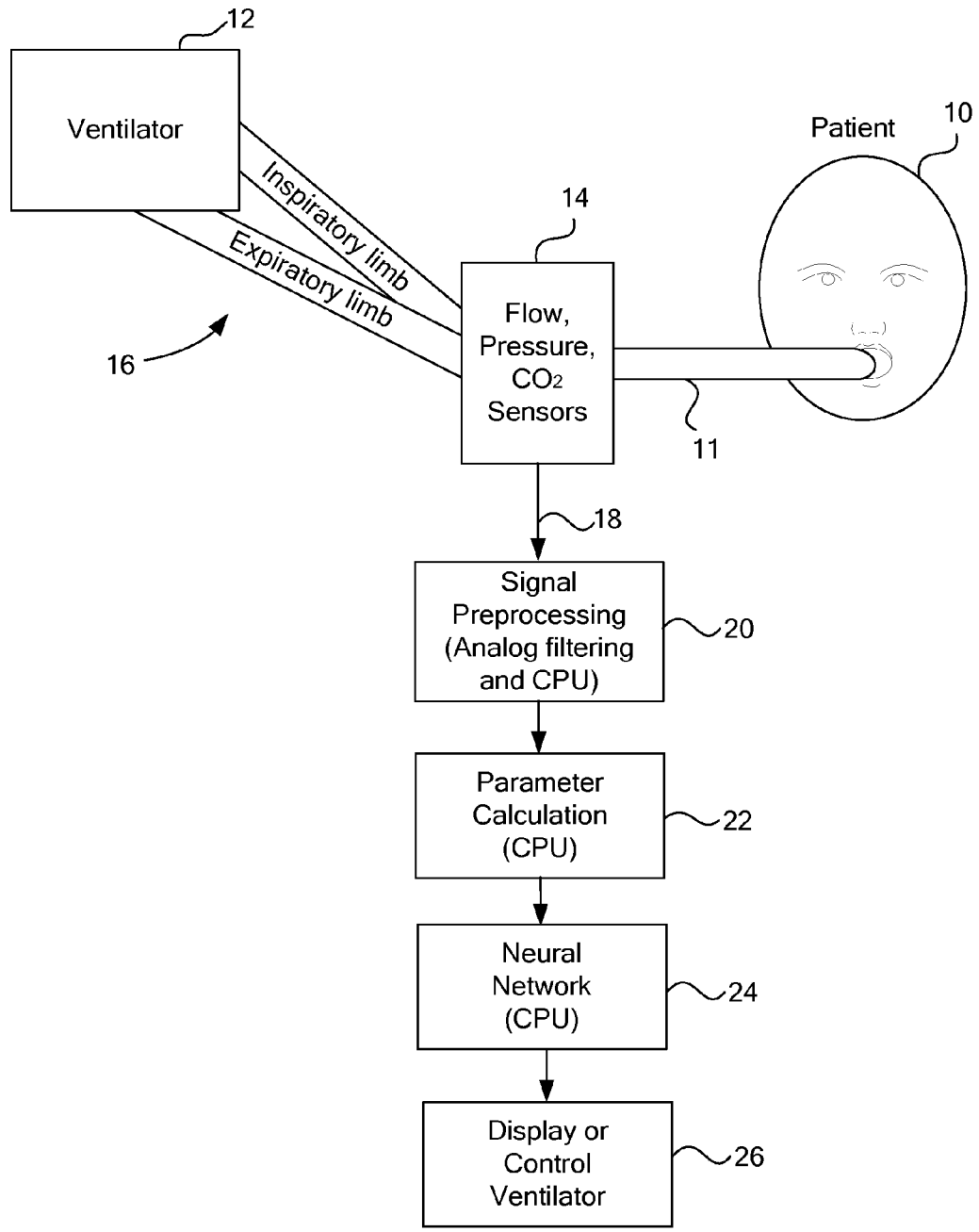
FIG. 2 depicts the method of one aspect of the invention for a patient on a ventilator.

In the embodiment depicted in FIG. 2, a patient 10 requiring respiratory support and connected to a ventilator 12 will have an airway flow and pressure sensor 14, along with possibly a carbon dioxide detector attached at the patient interface 11. Depending on the ventilator, an expiratory limb and/or inspiratory limb 16 can be present. The patient interface 11 can be invasive or noninvasive. For example, the patient interface can be a tube, a nasal mask or cannula, nasal prongs/pillows, a face mask, or other device for providing ventilation to a patient.

These sensors, e.g., 14, measure the flow, pressure, and partial pressure of carbon dioxide in the gases that pass to and from the patient. These raw signals 18 are preprocessed in a signal processor 20 using analog and digital signal processing to clean the signal, remove sensor biases and offsets, etc. These signals are then processed in a parameter extraction module 22 to calculate a variety of other parameters from the flow, pressure, and CO2 data. For example, tidal volume is computed by integrating the flow into the patient over an inspiratory cycle; peak inspiratory pressure is calculated by determining the maximum pressure during a breath; PO.1 is calculated by measuring the change in airway pressure during the first tenth of a second of a breath; respiratory system resistance and compliance can be calculated by adaptively fitting a model, such as a linear model, to the airway pressure, flow, and volume signals; etc. In an aspect of the invention, a neural network 24 may be provided to model the parameters so that a ventilator may be controlled through controller 26.

In order to create the model (training phase), patient information may be collected from one or more patients. The methodology of obtaining the test data (both input data and desired output data are used to create a model that will predict patient effort) is as follows:

An inflatable balloon is placed into the patient's esophagus and a catheter is placed in the patient's trachea. The balloon is partially inflated and creates a closed circuit that transmits esophageal pressure to a pressure sensor connected to the end of a catheter connected to the balloon. The pressure sensors read the tracheal pressure and the esophageal pressure, which is a surrogate for pleural pressure (FIG. 1). The esophageal pressure drop during normal breathing is plotted on a pressure-volume plot and a loop is created and integrated with a chest wall compliance line to calculate work of breathing. The esophageal pressure may be first cleaned of cardiac interference with an adaptive noise cancellation technique that subtracts a scaled and shifted version of the ECG or plethysmogram from the esophageal pressure. The chest wall compliance can he calculated by paralyzing the patient and measuring the esophageal pressure rise in the circuit with a positive pressure breath. Many studies have found that 0.1 L1 cm H2O is an appropriate average. This plot is called the Campbell diagram and is a method for calculating patient inspiratory or physiologic work of breathing from the measured esophageal pressure. For intubated patients, the imposed work of breathing may be calculated by integrating the tracheal pressure drop versus volume waveform similar to the total work of breathing (with the exception of the chest wall compliance). For both total and imposed efforts, power of breathing is calculated as a per minute average of work of breathing. Pressure Time Product (PTP) is measured just like WOB except using a Pressure-Time axis integration instead of Pressure-Volume. The work of breathing, (both physiologic and imposed), the power of breathing, and the pressure time product may be used as output variable for the system. These are the three main "desired outputs" of the preferred system. With patients using noninvasive ventilatory systems, the imposed work of breathing is not necessary for calculating work of breathing, power of breathing, and/or pressure time product.

Some of the inputs are standard parameters that are calculated in a very straight forward manner, such as spontaneous breathing frequency (the number of breaths the patient takes per minute), tidal volume (the volume of air inspired per breath), etc. Other input parameters are more complex, such as respiratory system resistance, compliance, and airway pressure waveform characteristics. Resistance and compliance for example, are typically calculated using a least squares modeling of the pressure, volume, and flow waveforms (obtained by a standard respiratory monitor using airway pressure and flow sensors) using the equation:

$$airway\_pressure = flow \times resistance + volume \times compliance + positive\_end\_expiratory\_pressure$$

Using the flow, volume, and pressure obtained from the flow and pressure sensors, the only unknowns are compliance and resistance and these can be adaptively computed using techniques such as least squares optimization, as noted above.

The problem with these methods is that the equation is only valid if the patient is not exerting any effort and the ventilator is responsible for all work of breathing. It has been experimentally determined that better results may be obtained by using an end-inspiratory pause and analyzing the pressure drop with the cessation of flow ($\Delta$airway_pressure/$\Delta$flow) as resistance, and the Tidal_volume/(airway_pressure−PEEP) after flow has ceased for the compliance. This method, however, is also inaccurate since often the patient's effort will disrupt the inspiratory pause. In an aspect of the invention, a method of calculating resistance and compliance may be based on examining the initial pressure rise during the very first few hundredths of a second for each breath. This initial pressure rise is related to only the flow entering the system as volume has not yet accumulated in the lung, and thus reflects only the resistance. After resistance is accurately modeled, compliance can be obtained more accurately with the standard least squares technique mentioned above.

In certain embodiments, particularly those where input parameters are collected via a non-invasive patient interface such as a mask or canula where circuit leaks are significant, compensation for leak flow is done to derive accurate flow, volume, and CO2 waveforms. In certain embodiments, pressure waveforms must also be corrected. When the leak is significant, the flow in and out of the patient is much different than that measured by the sensor since much of the air is lost through the leak. The goal of leak compensation is to accurately estimate the true values of the waveforms moving in and out of the patient. There are numerous methods for correcting for leak in a flow waveform including, but not limited to, (a) equally redistributing the measured lost volume over the breath and subtracting the bias flow from flow waveform, (b) calculating parabolic conductance and using the parabolic conductance to correct a measured flow waveform, (c) calculating the missing volume between inhalation and exhalation and allocating this volume throughout the breath, and (d) adjusting the flow waveform to minimize the average flow. Leak correction modifies the flow, volume, and CO2 waveforms on a sample by sample basis based on the parameters (e.g. parabolic conductance) calculated from the input waveforms. These parameters can be calculated and adjusted continuously on a sample by sample basis, or calculated periodically based on a windowing approach that may include overlap in the windows.

During data collection for the training data, the ventilator is adjusted; for example, the pressure support level may be adjusted and measured work of breathing and the other parameters are continuously monitored while changing the ventilator. Stable regions of the data are saved and parameters are averaged over 1-2 minutes to reduce the noise inherent in biological signals and the breath-to-breath variations. These averaged parameters are then used to create the model.

In an embodiment, the model, such as a neural network, is pretrained with clinical data and the input parameters can be collected noninvasively with a standard respiratory monitor.

A neural network is trained to predict the physiologic and imposed WOB, POB, and PTP using the noninvasively acquired parameters described above (although invasive parameters may be added to the system, if desired.) Once a model having a desired degree of predictability has been achieved and verified, the esophageal pressure data (WOB, POB, PTP) is no longer needed and the network output, such as an actual breathing effort variable, may be used as an accurate predictor of patient effort.

Description of Neural Networks

Artificial neural networks loosely model the functioning of a biological neural network, such as the human brain. Accordingly, neural networks are typically implemented as computer simulations of a system of interconnected neurons. In particular, neural networks are hierarchical collections of interconnected processing elements (PEs). These elements are typically arranged in layers, where the input layer receives the input data, the hidden layers transform the data, and the output layer produces the desired output. Other embodiments of a neural network can also be used.

Each processing element in the neural network receives multiple input signals, or data values, that are processed to compute a single output. The inputs are received from the outputs of PEs in the previous layer or from the input data. The output value of a PE is calculated using a mathematical equation, known in the art as an activation function or a transfer function that specifies the relationship between input data values. As known in the art, the activation function may include a threshold, or a bias element. The outputs of elements at lower network levels are provided as inputs to elements at higher levels. The highest level element, or elements, produces a final system output, or outputs.

Figure 4:
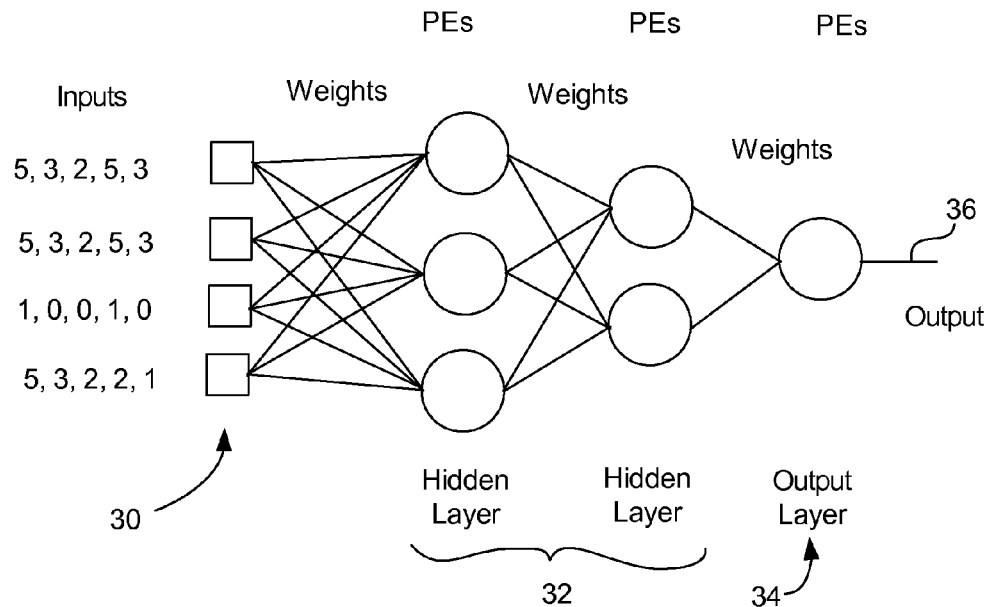
FIG. 4 depicts a neural network showing hidden layers.

In the context of the present invention, the neural network is a computer simulation that is used to produce a noninvasive estimate of the quantified patient effort described previously. The neural network of the present invention may be constructed by specifying the number, arrangement, and connection of the processing elements which make up the network. A simple embodiment of a neural network consists of a fully connected network of processing elements. As shown in FIG. 4, the processing elements of the neural network are grouped into the following layers: an input layer 30 where the parameters collected and/or derived from the airway pressure and flow sensors are inputted to the network; a hidden layer or layers 32 of processing elements; and an output layer 34 where the resulting prediction of patient effort 36 is produced. The number of connections, and consequently the number of connection weights, is fixed by the number of elements in each layer 30, 32, 34.

Figure 5:
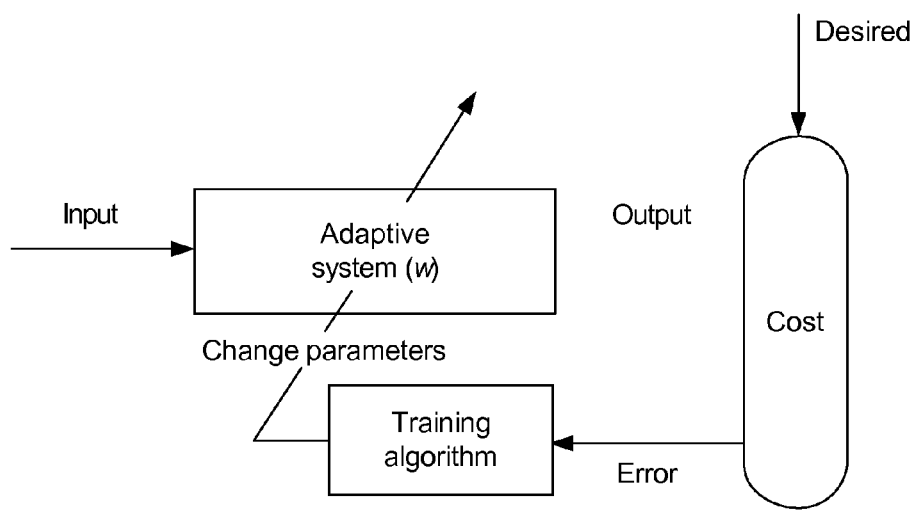
FIG. 5 depicts inputs and outputs of an adaptive system having backpropagation.

The most common training methodology for neural networks is based upon iterative improvement of the system parameters (normally called weights) by minimizing the mean squared difference between the desired output and the network output (mean squared error, MSE). The input is applied to the neural network, the neural network passes the data through its hierarchical structure, and an output is created. This network output is compared with the desired output corresponding to that input and an error is calculated. This error is then used to adjust the weights of the system so that the next time that particular input is applied to the system the network output will be closer to the desired output. There are many possible methodologies to adjust the weights, called the training algorithm. As shown in FIG. 5, the most common is called backpropagation that involves calculating each weight's responsibility for the error, and calculating a local gradient from this error in order to use a gradient descent learning rule for each weight.

Based on the foregoing specification, the invention may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the invention. The computer readable media may be, for instance, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network.

One skilled in the art of computer science will easily be able to combine the software created as described with appropriate general purpose or special purpose computer hardware to create a computer system or computer sub-system embodying the method of the invention. An apparatus for making, using or selling the invention may be one or more processing systems including, but not limited to, a central processing unit (CPU), memory, storage devices, communication links and devices, servers, I/O devices, or any subcomponents of one or more processing systems, including software, firmware, hardware or any combination or subset thereof, which embody the invention. User input may be received from the keyboard, mouse, pen, voice, touch screen, or any other means by which a human can input data into a computer, including through other programs such as application programs.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Prediction of Power of Breathing

Figure 3:
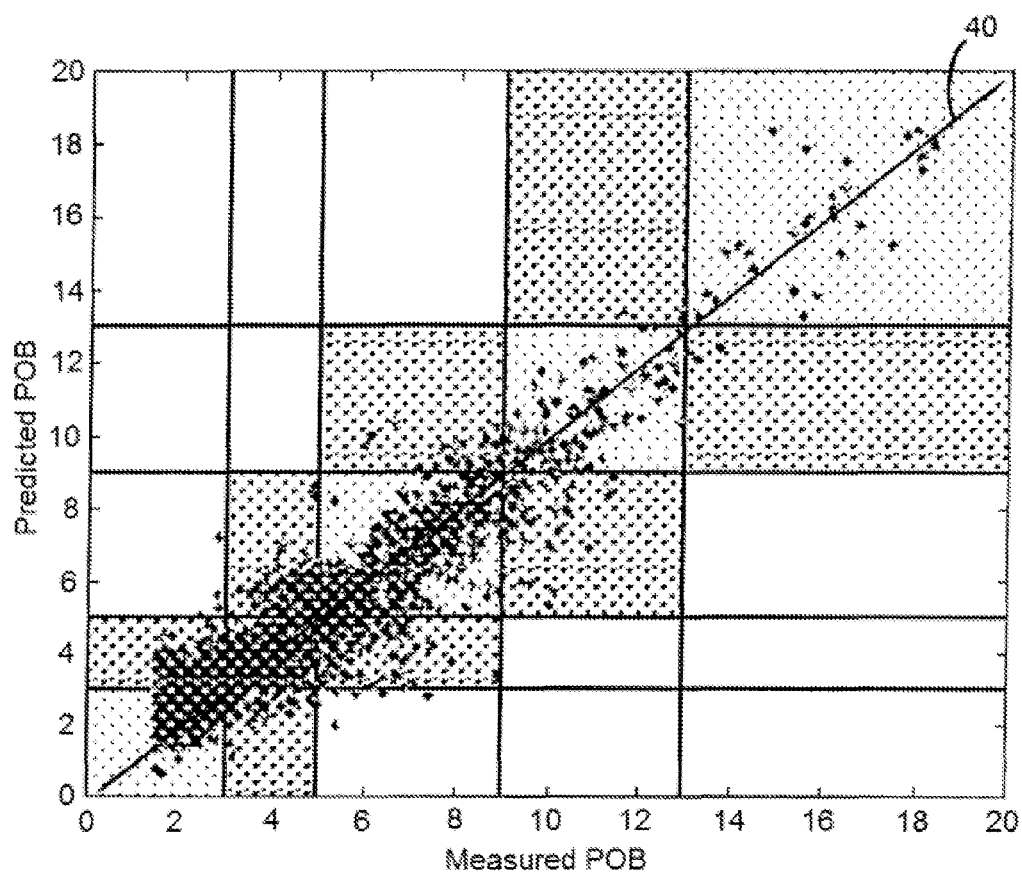
FIG. 3 depicts a graph of the nonlinear prediction of Power of Breathing.

With one particular subset of parameters (respiratory system resistance, compliance, tidal volume, and frequency), the present invention predicted power of breathing with a correlation coefficient well over 0.90. Similar results were obtained with other combinations of parameters. FIG. 3 shows a plot of predicted versus actual, or measured, power of breathing. A perfect prediction would be indicated by all values having identical x- and y-axis values, and thus would fall on the diagonal black line 40 shown in the FIG. 3. The wider the spread from this line, the lower the correlation between predicted and actual power of breathing. In this particular prediction, data was obtained from 150 patients collected at Shands Hospital at the University of Florida. The data was collected with multiple ventilator settings for each patient, thus giving us approximately 500 data points in the study.

EXAMPLE 2

Data for a Prediction (Table 1 Includes the First Data Points)

During data collection, respiratory measurements are made continuously and collected. These measurements are stored and later fed to the neural network for training. After the neural network model is trained successfully, the measurements from future are input to the "trained" model to produce a noninvasive prediction of actual power of breathing. This prediction of power of breathing is then used in a downstream fuzzy logic system that recommends changes to the ventilator.

In this example, the inputs/outputs to the system are:

Minute Ventilation—the total volume delivered to the patient per minute (e.g. roughly tidal volume times breath frequency) in Liters.

Trigger Gradient—the slope of the airway pressure drop due to the patient effort that riggers the breath (e.g. before the ventilator starts providing flow to the patient) in cm H2O per second.

Pressure Rise Time—the time it takes for the flow to reach a maximum and then decay to 80% of the maximum during a PSV(pressure support ventilation) breath, as a proportion of total inspiratory time (no units).

Pmus using R Spike—the muscle pressure (as described in the patent) using the resistance measurement from the initial time of pressure rise (as described in the patent) and using the least squares compliance (cm H2O*sec).

Actual POE—the power of breathing (work per minute) measured (Joules/min),

Predicted POB—the power of breathing predicted by the system (Joules/min).

These numbers were recorded continuously with data collection software. The values coming from the sensors are smoothed (time constant of roughly 2 minutes) and analyzed continuously as known in the art. When no errors, artifacts, or transients are detected, a set of parameters is labeled as "suitable for prediction", at one set of parameters per minute. These numbers are then collected and used to train the neural network. The neural network output is then used to optimally set the ventilator based on the predicted power of breathing and other relevant patient parameters (such as breathing frequency, tidal volume, and end-tidal CO2).

TABLE 1

| Minute Ventilation | Trigger Gradient | Pressure Rise Time | pmus using R Spike | Actual POB | Predicted POB |
| --- | --- | --- | --- | --- | --- |
| 8.2 | 14.2 | 0.8 | 63.4 | 3.2 | 4.1 |
| 7.1 | 6.4 | 0.7 | 40.7 | 2.6 | 2.7 |
| 8.5 | 15.3 | 0.8 | 72.9 | 5.9 | 6.2 |
| 11.9 | 9.5 | 0.8 | 81.2 | 6.5 | 6.2 |
| 7.9 | 8.0 | 0.9 | 37.7 | 4.6 | 5.8 |
| 7.7 | 12.4 | 0.9 | 64.3 | 7.2 | 6.5 |
| 8.4 | 13.4 | 0.5 | 51.5 | 2.1 | 2.1 |
| 7.8 | 8.1 | 0.7 | 79.4 | 3.8 | 3.4 |
| 4.9 | 15.2 | 0.8 | 41.5 | 5.5 | 5.0 |
| 6.3 | 26.3 | 0.8 | 41.4 | 5.4 | 5.7 |
| 6.1 | 2.3 | 0.7 | 37.3 | 1.5 | 2.0 |
| 11.0 | 15.4 | 0.9 | 83.5 | 8.9 | 9.0 |
| 9.9 | 7.5 | 0.7 | 74.2 | 2.0 | 3.2 |

TABLE 1-continued

| Minute Ventilation | Trigger Gradient | Pressure Rise Time | pmus using R Spike | Actual POB | Predicted POB |
| --- | --- | --- | --- | --- | --- |
| 4.5 | 8.1 | 0.8 | 47.3 | 3.8 | 3.2 |
| 5.6 | 3.4 | 0.7 | 21.8 | 1.6 | 2.3 |
| 6.3 | 12.0 | 0.9 | 77.0 | 6.4 | 5.8 |
| 11.7 | 11.2 | 0.8 | 66.4 | 6.5 | 7.0 |
| 3.1 | 12.9 | 0.7 | 31.3 | 2.8 | 2.4 |
| 7.1 | 2.0 | 0.7 | 15.0 | 2.9 | 2.3 |
| 8.0 | 7.4 | 0.7 | 79.5 | 3.8 | 3.4 |
| 7.8 | 4.4 | 0.7 | 22.1 | 2.6 | 2.5 |
| 12.1 | 26.3 | 0.8 | 179.2 | 13.4 | 11.4 |
| 6.3 | 6.4 | 0.7 | 21.4 | 2.2 | 2.7 |
| 5.7 | 18.3 | 0.8 | 31.1 | 5.3 | 5.4 |
| 7.8 | 10.9 | 0.5 | 73.9 | 3.1 | 2.5 |
| 8.1 | 6.1 | 0.8 | 56.5 | 4.3 | 3.7 |
| 7.0 | 16.6 | 0.8 | 69.5 | 5.0 | 5.6 |
| 4.6 | 13.5 | 0.7 | 26.9 | 4.0 | 3.0 |
| 6.9 | 10.9 | 0.8 | 29.4 | 3.5 | 5.0 |
| 4.8 | 14.0 | 0.8 | 39.7 | 5.3 | 4.8 |
| 8.2 | 33.5 | 0.5 | 95.5 | 1.7 | 2.8 |
| 9.9 | 11.4 | 0.8 | 35.6 | 6.9 | 5.9 |
| 5.6 | 18.5 | 0.6 | 30.2 | 4.6 | 3.7 |
| 5.5 | 12.1 | 0.8 | 49.5 | 5.5 | 4.9 |
| 8.1 | 12.4 | 0.8 | 82.0 | 3.8 | 4.3 |
| 6.5 | 16.0 | 0.9 | 46.0 | 3.4 | 5.4 |
| 11.5 | 16.7 | 0.8 | 45.9 | 9.1 | 9.7 |
| 7.9 | 9.3 | 0.8 | 59.0 | 3.9 | 4.7 |
| 9.1 | 7.6 | 0.6 | 47.4 | 1.5 | 2.5 |
| 8.5 | 4.0 | 0.6 | 32.0 | 1.7 | 2.2 |
| 6.2 | 13.6 | 0.6 | 33.1 | 5.1 | 3.3 |
| 7.1 | 21.6 | 0.8 | 77.6 | 5.7 | 5.2 |
| 8.3 | 13.7 | 0.9 | 87.6 | 8.3 | 6.8 |
| 6.6 | 25.2 | 0.8 | 38.8 | 4.8 | 5.7 |
| 6.4 | 19.2 | 0.7 | 36.5 | 5.1 | 5.1 |
| 12.5 | 12.8 | 0.9 | 93.4 | 9.2 | 9.9 |
| 8.9 | 14.7 | 0.7 | 71.2 | 3.1 | 3.9 |

It should be understood that the examples and embodiments described herein are for illustrative purposes only and that various modifications or changes in light thereof will be suggested to persons skilled in the art and are to be included within the spirit and purview of this application and the scope thereof.

What is claimed is:

1. A method for estimating effort of breathing of a patient, comprising:

collecting noninvasive respiratory parameters of the patient, while receiving mechanical ventilation;

calculating, using a processor, respiratory data from the respiratory parameters;

inputting the respiratory data into a mathematical model created using clinical data from a population of patients, where the clinical data includes pleural pressure or a surrogate of pleural pressure; and generating at least one output variable using the mathematical model corresponding to an estimated effort of breathing, wherein the estimated effort of breathing is an estimate of the patient's actual effort of breathing throughout an entire breath, and wherein the at least one output variable is generated by the processor configured to run the mathematical model.

2. The method of claim 1 wherein effort of breathing represents a physiologic work of breathing and an imposed work of breathing.

3. The method of claim 1 wherein the respiratory parameters comprise one or more of airway pressure, airway flow, airway volume, carbon dioxide flow, leak flow, and pulse oximeter plethysmogram.

4. The method of claim 3, wherein compensation for leak flow is performed before the respiratory data are calculated.

5. The method of claim 4, wherein the compensation for leak flow is calculated from a step selected from the group consisting of: (a) equally redistributing a measured lost volume over a breath and subtracting a bias flow from a measured flow waveform, (b) calculating a parabolic conductance and using the parabolic conductance to correct the measured flow waveform, (c) windowing the calculation of parabolic conductance for real-time correction of the measured flow waveform, and (d) calculating the parabolic conductance using a breath detector that functions to detect a start and end of each breath to generate the parabolic conductance that is applied to the measured flow waveform.

6. The method of claim 1, wherein the mathematical model is selected from the group consisting of a neural network model, a fuzzy logic model, a mixture of experts model, or a polynomial model.

7. The method of claim 1, wherein the respiratory data comprises one or more of tidal volume, breathing frequency, peak inspiratory pressure, inspiratory time, occlusion pressure at 0.1 seconds after breath initiation trigger time, trigger depth, respiratory resistance, respiratory compliance, end-tidal carbon dioxide, variations in the pulse oximeter plethysmogram, and concavity/convexity of a pressure waveform.

8. The method of claim 1, wherein the mechanical ventilation is delivered via an invasive or noninvasive ventilator.

9. The method of claim 8, wherein the noninvasive ventilator comprises a patient interface assembly selected from the group consisting of: a tube, a nasal mask, a nasal/oral mask, a total face mask, a nasal cannula, and nasal prongs/pillows.

10. The method of claim 1, further comprising providing said at least one output variable from the mathematical model to a ventilator to adjust a ventilator setting.

11. The method of claim 1, further comprising providing the output variable from the mathematical model corresponding to effort of breathing to a display.

12. The method of claim 1, wherein the output variable comprises one or more of a physiologic work of breathing variable, an imposed work of breathing variable, a power of breathing variable, and a pressure time product variable, each representing the effort exerted by the patient to breathe.

13. The method of claim 1, wherein the mathematical model is a neural network trained to provide said at least one output variable, wherein the training of the neural network comprises clinical testing of a test population of patients using esophageal pressure as clinical data input to the neural network.

14. The method of claim 13, wherein a drop in esophageal pressure is plotted on a pressure-volume plot and a loop is created and integrated with chest wall compliance line to calculate inspiratory work of breathing as one of said output variables.

15. The method of claim 14, wherein the approximation of 0.1 L/cm H20 is used for chest wall compliance.

16. The method of claim 14, further comprising calculating power of breathing as a per- minute average of work of breathing as one of said output variables.

17. The method of claim 14, further comprising calculating Pressure Time Product (PTP) as one of said output variables.

18. The method of claim 1, further comprising:
classifying the patient; and
selecting the mathematical model based on a classification of the patient.

19. The method of claim 18, wherein the patient is classified according to pathophysiology and physiologic parameters related to the patient.

20. The method of claim 19, wherein the physiologic parameters comprise lung resistance and compliance.

21. An apparatus for estimating effort of breathing of a patient, comprising:
a processing device for calculating respiratory data derived from noninvasive respiratory parameters of a patient receiving mechanical ventilation, wherein the noninvasive respiratory parameters comprise one or more of airway pressure, airway flow, airway volume, carbon dioxide flow, leak flow and pulse oximeter plethysmogram, and wherein the respiratory data comprises one or more of tidal volume, breathing frequency, peak inspiratory pressure, inspiratory time, occlusion pressure at 0.1 seconds after breath initiation trigger time, trigger depth, respiratory resistance, respiratory compliance, end-tidal carbon dioxide, variations in the pulse oximeter plethysmogram, and concavity/convexity of a pressure waveform;
a mathematical modeling device, created using clinical data from a population of patients, wherein the clinical data includes pleural pressure or a surrogate of pleural pressure, to receive the respiratory data and predict effort of breathing; and
an output signal that provides at least one output variable from the mathematical model corresponding to effort of breathing.

22. The apparatus of claim 21, wherein the mathematical modeling device is a neural network trained to provide said at least one output variable, wherein the training of the neural network comprises clinical testing of a test population of patients.

23. The apparatus of claim 21, wherein the output variable comprises one or more of a physiologic work of breathing variable, an imposed work of breathing variable, a power of breathing variable, and a pressure time product variable, each representing the effort exerted by the patient to breathe.

24. The apparatus of claim 21, wherein the mechanical ventilation is delivered via a noninvasive ventilator that comprises a patient interface assembly selected from the group consisting of: a tube, a nasal mask, a nasal/oral mask, a total face mask, a nasal cannula, and nasal prongs/pillows.

25. A system for estimating effort of breathing of a patient, comprising:
means for collecting noninvasive respiratory parameters of the patient receiving mechanical ventilation, wherein the noninvasive respiratory parameters comprise one or more of airway pressure, airway flow, airway volume, carbon dioxide flow, leak flow and pulse oximeter plethysmogram;
means for calculating respiratory data from the respiratory parameters, wherein the respiratory data comprises one or more of tidal volume, breathing frequency, peak inspiratory pressure, inspiratory time, occlusion pressure at 0.1 seconds after breath initiation trigger time, trigger depth, respiratory resistance, respiratory compliance, end-tidal carbon dioxide, variations in the pulse oximeter plethysmogram, and concavity/convexity of a pressure waveform;
means for predicting effort of breathing using a mathematical model created using clinical data from a population of patients, wherein the clinical data includes pleural pressure or a surrogate of pleural pressure, that receives the respiratory data; and
means for providing at least one output variable from the mathematical model corresponding to effort of breathing.

26. The system of claim 25, wherein the mathematical model is a neural network trained to provide said at least one output variable, wherein the training of the neural network comprises clinical testing of a test population of patients.

27. The system of claim 25, wherein the output variable comprises one or more of a physiologic work of breathing variable, an imposed work of breathing variable, a power of breathing variable, and a pressure time product variable, each representing the effort exerted by the patient to breathe.

28. The system of claim 25, wherein the mechanical ventilation is delivered via a noninvasive ventilator that comprises a patient interface assembly selected from the group consisting of: a nasal mask, a nasal/oral mask, a total face mask, a nasal cannula, and nasal prongs/pillows.

29. A non-transitory computer readable medium for estimating effort of breathing of a patient, comprising:
   code devices for receiving measured noninvasive respiratory parameters of the patient receiving mechanical ventilation, wherein the noninvasive respiratory parameters comprise one or more of airway pressure, airway flow, airway volume, carbon dioxide flow, leak flow and pulse oximeter plethysmogram;
   code devices for calculating respiratory data from the respiratory parameters, wherein the respiratory data comprises one or more of tidal volume, breathing frequency, peak inspiratory pressure, inspiratory time, occlusion pressure at 0.1 seconds after breath initiation trigger time, trigger depth, respiratory resistance, respiratory compliance, end-tidal carbon dioxide, variations in the pulse oximeter plethysmogram, and concavity/convexity of a pressure waveform;
   code devices for predicting effort of breathing using a mathematical model created using clinical data from s population of patients, wherein the clinical data includes pleural pressure or a surrogate of pleural pressure, that receives the respiratory data; and
   code devices for providing at least one output variable from the mathematical model corresponding to effort of breathing.

30. The computer readable medium of claim 29, wherein the mathematical model is a neural network trained to provide said at least one output variable, wherein the training of the neural network comprises clinical testing of a test population of patients.

31. The computer readable medium of claim 29, wherein the output variable comprises one or more of a physiologic work of breathing variable, an imposed work of breathing variable, a power of breathing variable, and a pressure time product variable, each representing the effort exerted by the patient to breathe.

* * * * *

UNITED STATES PATENT AND TRADEMARK OFFICE
CERTIFICATE OF CORRECTION

PATENT NO. : 8,672,858 B2  
APPLICATION NO. : 13/400371  
DATED : March 18, 2014  
INVENTOR(S) : Neil Russell Euliano et al.

Page 1 of 1

It is certified that error appears in the above-identified patent and that said Letters Patent is hereby corrected as shown below:

In the Specification

Column 2,
Line 12, "("WOW")" should read --("WOB")--.

Column 7,
Line 44, "can he calculated" should read --can be calculated--.

Column 11,
Line 25, "that riggers" should read --that triggers--.

Signed and Sealed this
First Day of July, 2014

Michelle K. Lee
*Deputy Director of the United States Patent and Trademark Office*